United States Patent
Eguchi et al.

(10) Patent No.: US 8,344,332 B2
(45) Date of Patent: Jan. 1, 2013

(54) ELECTRON BEAM IRRADIATION APPARATUS FOR STERILIZING SHEET MATERIAL

(75) Inventors: Shiro Eguchi, Chiba (JP); Tomoyuki Hikosaka, Ichihara (JP); Satoru Gohzaki, Ichihara (JP); Takayuki Suzuki, Kisarazu (JP); Shigekatsu Sato, Hitachi (JP); Isao Hashimoto, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 5 days.

(21) Appl. No.: 12/992,084

(22) PCT Filed: May 12, 2008

(86) PCT No.: PCT/JP2008/059095
§ 371 (c)(1),
(2), (4) Date: Nov. 10, 2010

(87) PCT Pub. No.: WO2009/139073
PCT Pub. Date: Nov. 19, 2009

(65) Prior Publication Data
US 2011/0062347 A1  Mar. 17, 2011

(51) Int. Cl.
B65B 55/08  (2006.01)

(52) U.S. Cl. .................. 250/455.11; 250/492.3

(58) Field of Classification Search .......... 250/455.11, 250/492.3, 503.1
See application file for complete search history.

(56) References Cited

U.S. PATENT DOCUMENTS

| | | | | |
|---|---|---|---|---|
| 3,418,155 A | * | 12/1968 | Colvin et al. | 427/551 |
| 6,132,817 A | * | 10/2000 | Tokutake et al. | 427/578 |
| 7,767,987 B2 | * | 8/2010 | Eguchi et al. | 250/492.3 |
| 2010/0221155 A1 | * | 9/2010 | Shimizu et al. | 422/186.05 |

FOREIGN PATENT DOCUMENTS

| | | |
|---|---|---|
| GB | 1286824 | 8/1972 |
| JP | 4724654 | 7/1972 |
| JP | 498930 | 3/1974 |
| JP | 60-99829 | 6/1985 |
| JP | 11119000 | 4/1999 |
| JP | 2001242297 | 9/2001 |
| JP | 2003054521 | 2/2003 |
| JP | 2004/524895 | 8/2004 |
| JP | 2007-113936 | 5/2007 |
| WO | WO 02/066081 | 8/2002 |

OTHER PUBLICATIONS

International Search Report in International Application No. PCT/JP2008/059095 mailed Aug. 5, 2008.
Japanese Office Action issued in JP 2007-074329, mailed May 22, 2012 with English language translation.
Japanese Office Action issued in JP 2007-074329, mailed Dec. 27, 2011 with English language translation.

* cited by examiner

*Primary Examiner* — Kiet T Nguyen
(74) *Attorney, Agent, or Firm* — Brundidge & Stanger, P.C.

(57) ABSTRACT

At a conveying path 10 for continuously carrying a sheet material 1, an electron beam irradiation means 20 is arranged in opposition to at least one surface of the sheet material 1, and at least one surface of the sheet material 1 is sterilized using such an electron beam. The conveying path 10 takes shape of a hollow box surrounding the sheet material, and has an electron beam irradiation area 11 at a part of this area, while keeping a reduced-pressure state ranging from 10 to 80,000 Pa using a pressure reduction means 16. Further, the electron beam irradiation area 11 where the electron beam irradiation means 20 is arranged at least one sub area 12 at each of adjacent hollow box-shaped conveying path 10 at carry-in side and carry-out side of the sheet material, providing the pressure reduction means 16 for depressurizing the sub area 12.

2 Claims, 4 Drawing Sheets

ELECTRON BEAM IRRADIATION APPARATUS FOR STERILIZING SHEET MATERIAL

TECHNICAL FIELD

The present invention relates to an electron beam irradiation apparatus for sterilization of a sheet material and more particularly to such an electron beam irradiation apparatus for sterilization of a sheet material as is suitable for electron beam sterilization of a sheet material to be used for forming containers for packing liquid food like beverages.

BACKGROUND ART

As a usual method, a paper-made container (hereinafter referred to as "cartons") is widely used for packing liquid food like milk and juice. A sheet material for the carton is made by combining a cardboard made from pulp or similar raw material with a thin layer of heat-sealable plastic thereon or instead with a layer of aluminum foil thereon to keep liquid food in a sealed state for more extended period of time. These layers are laminated on at least such a surface of the cardboard as will become inner surface of a carton to which liquid food contacts when the cardboard is formed into the carton.

As commonly known, carton-packed food is shipped from a packing plant in the following manner: A sheet material in roll loaded on a payoff device is fed continuously into a carton forming line, in which line the sheet material is sized as designed and then folded into a desired shape of carton by a folding means. In the successive process, liquid food is filled into the carton thus formed and the filling port of the carton is sealed to complete packing process.

The sheet material for cartons is sterilized while travelling from the payoff device to the cartoning line and is transferred aseptically, a germfree condition without contamination, into the subsequent process.

Sterilization of sheet material conventionally used chemicals. This method however requires large scaled installations. Moreover, such method involves an anxiety about chemical residue on the sheet material sterilized. This anxiety therefore demands a process for a complete removal of chemicals from the sheet material. Consequently, an improvement has been desired in a sterilization device applicable to liquid food handling.

As a solution to this problem, an invention has been disclosed in JP2004-524895A1 (Patent Literature 1), which is known as a late alternative to a chemical sterilization apparatus for a sheet material. In Patent Literature 1, a unit for sterilization is proposed. The proposed unit is feasible for downsizing and efficiently sterilizes both surfaces of a sheet material with electron beam generated from an electron beam irradiation means while the sheet material is in high-speed transferring.

More specifically, the electron beam irradiation unit for sterilizing a sheet material defined in Patent Literature 1 has two electron beam irradiation means arranged across the sheet material facing each other in a part of a conveying path in the atmosphere. This arrangement radiates electron beam from each of the electron beam irradiation means to the sheet material in a high-speed transferring to sterilize both surfaces of the sheet material with electron beam. The sheet material thus sterilized is then transferred to the next stage of processing. Each of the electron beam irradiation means that generates low-energy electron beam accelerated at a voltage below 100 kV has its electron beam source enclosed by a vessel and has radiation shielding material such as lead plate installed inner wall of the vessel as a measure against X-rays that the electron beam source emits.

The above-stated electron beam irradiation unit for sterilizing a sheet material of a conventional style is able to efficiently sterilize both surfaces of sheet material. The unit however has a problem in that the unit is not compatible with such an electron beam irradiation means as works on a lower energy because such unit uses the electron beam irradiation means in the atmosphere in which electron beam having larger energy to certain degree is essential to sterilize.

Further, an electron beam irradiation means used in the atmosphere must have a radiation shielding material to shield X-rays emitted from the electron beam source of the irradiation means. This requirement results in a size-growth of the sterilization equipment as a whole possibly preventing the right positioning of the irradiation means on the sheet material conveying path.

Moreover, an electron beam irradiation means for use in the atmosphere easily generates plasma, which produces ozone ($O_3$) from oxygen in the air.

The produced ozone, adhering to the sheet material sterilized, makes the sheet smell like ozone. Such smelling sheet material is not appropriate to a carton for liquid food packing. To remove the ozone odor, a measure such as lowering the oxygen concentration in the irradiation chamber by blowing nitrogen gas thereinto while electron beam irradiation is necessary; this arrangement makes the sterilization equipment sophisticated.

The object of the present invention is to provide an electron beam irradiation apparatus for sterilization of a sheet material. The device efficiently sterilizes at least one surface of a sheet material for a carton using a low-energy electron beam irradiation means under an appropriately regulated reduced-pressure atmosphere generating no ozone.

DISCLOSURE OF INVENTION a conveying path for transferring a sheet material continuously; an electron beam irradiation means arranged on the conveying path so as to face at least one surface of the sheet material; the conveying path being given a hollow box-shape that encloses the sheet material under sterilization of both surfaces thereof by electron beam from the electron beam generation means; the electron beam irradiation means arranged on an electron beam irradiation area in a part of the conveying path, a pressure reduction means, in which the electron beam irradiation area is maintained in a reduced-pressure state from 10 to 10,000 Pa by the pressure reduction means, and at least one sub area provided respectively on the carry-in side and the carry-out side of the sheet material on the hollow box-shaped conveying path adjacent to the electron beam irradiation area, and a pressure reduction means reduces the pressure of the sub area.

It is a preferable feature to form the sub area with a partition wall fixed inside the conveying path and a roller that carries the sheet material.

Another electron beam irradiation apparatus for sterilizing sheet material by the present invention has conveying path for transferring a sheet material continuously; an electron beam irradiation means arranged on the conveying path so as to face at least one surface of the sheet material; the conveying path being given a hollow box-shape that encloses the sheet material under sterilization of both surfaces thereof by electron beam from the electron beam generation means; the electron beam irradiation means arranged on an electron beam irradiation area in a part of the conveying path, a pressure reduction means; and a clean air supply means, in which the electron beam irradiation area is maintained in a reduced-pressure state from 10 to 10,000 Pa by the pressure reduction means, and at least one sub area provided respectively on the carry-in side and the carry-out side of the sheet material on the hollow box-shaped conveying path adjacent to the electron beam irradiation area, and the pressure reduction means reduces the internal pressure of the sub area, a gas area located at least on the outer side of the sub area of the carry-out side of the hollow box-shaped conveying path at the farthest location from the electron beam irradiation area; and the clean air supply means feeds clean air to the gas area at a pressure higher than the atmosphere.

It is a preferable feature to form the sub area and the gas area with partition walls fixed inside the conveying path and rollers that carry the sheet material.

EFFECT OF INVENTION

Composing an electron beam irradiation apparatus for sterilizing sheet material as defined in the present invention causes the sheet material to be sterilized at least one surface thereof with electron beam irradiation in the electron beam irradiation area kept in a reduced-pressure state of 10 Pa to 10,000 Pa. Therefore, the sterilization is well performed using a low-energy electron beam irradiation means.

Further, this irradiation in a reduced-pressure state of 10 Pa to 10,000 Pa is suitable for sterilization of sheet material for food packing because the electron beam irradiation means generates no ozone in that pressure. Moreover, X-ray shield for the electron beam irradiation area or for the electron beam irradiation means can be simplified or omitted because the electron beam irradiation means generates remarkably small X-rays. Therefore, the electron beam irradiation apparatus for sterilizing sheet material can be manufactured economically.

Additionally, an electron beam irradiation apparatus for sterilizing sheet material by the present invention further has a gas area located at least on the outer side of the sub area of the carry-out side of the hollow box-shaped conveying path at the farthest location from the electron beam irradiation area and a clean air supply means that feeds clean air to the gas area. This configuration prevents germ invasion into the hollow box-shaped conveying path from the outside around the sheet material carry-out area. Therefore, it becomes practicable to transfer the sheet material to the subsequent process maintaining well-sterilized condition after being sterilized with electron beam. Thus, the invented device is highly effective in applying to a carton manufacturing line into which liquid food is filled.

BEST MODE FOR CARRYING OUT THE INVENTION

Figure 1:
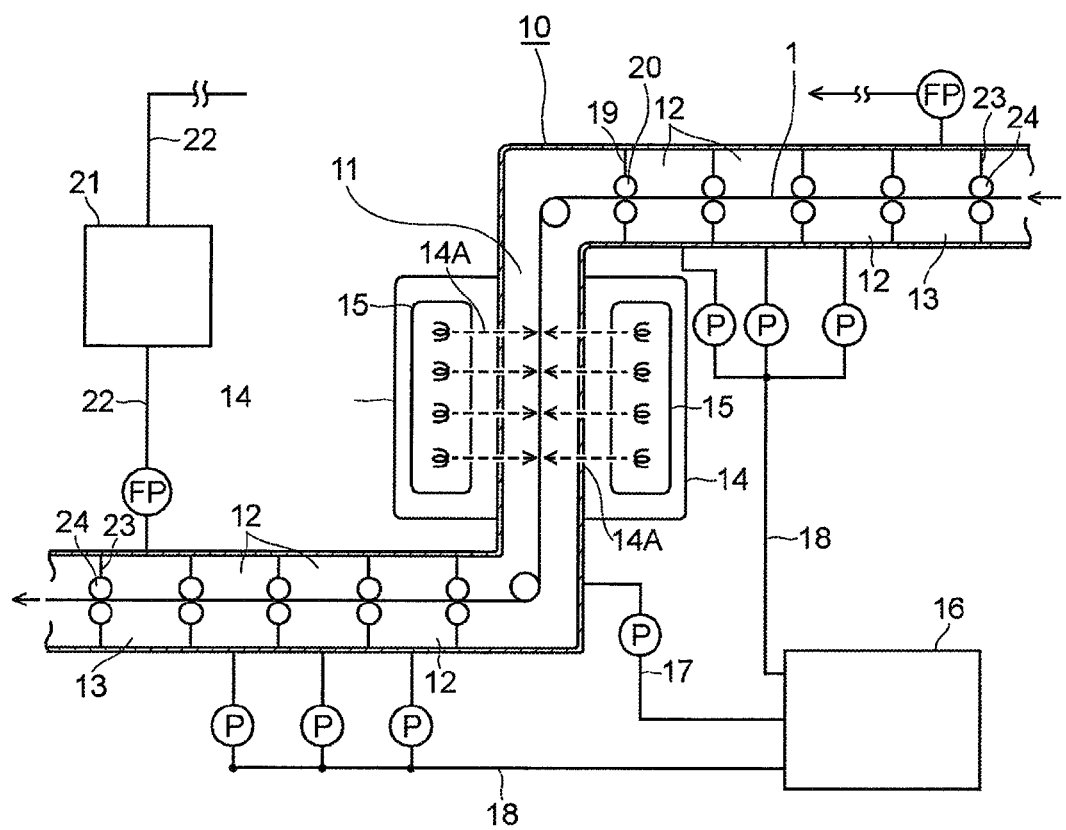
FIG. 1 is a schematic illustration of an electron beam irradiation apparatus for sterilizing sheet material as an embodiment of the present invention.
Figure 2:
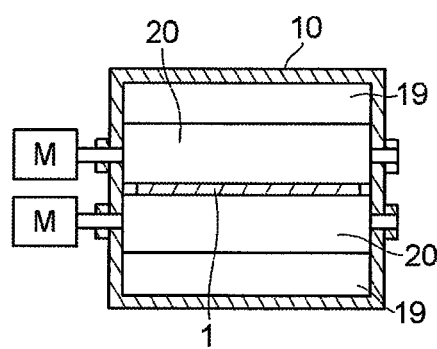
FIG. 2 is a schematic vertical sectional illustration of an example of a hollow box-shaped conveying path to be used in the electron beam irradiation apparatus for sterilizing sheet material by the present invention.
Figure 3:
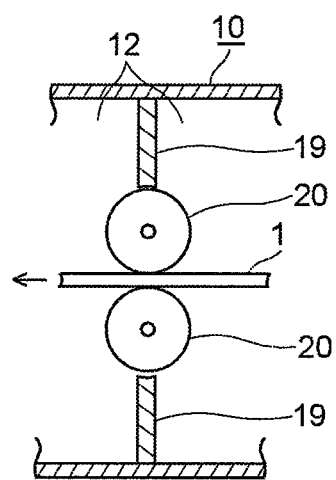
FIG. 3 is a sectional side view of the example of a hollow box-shaped conveying path illustrated in FIG. 2.

The following explains an example of electron beam irradiation apparatus for sterilizing sheet material by the present invention referring to FIGS. 1 to 3.

FIG. 1 illustrates a part of manufacturing process of a carton into which liquid food is filled. A conveying path 10 is given a hollow box-shape of metal plate such as stainless steel enveloping the sheet material and has such a structure that inside thereof is separable from the atmosphere. The sheet material supplied form a payoff device (not illustrated) is transferred through this hollow box-shaped conveying path 10 at a high-speed.

A part of the conveying path 10 is defined to be an electron beam irradiation area 11, which is connected to a pressure reduction means 16 like a vacuum device via an exhaust system 17 that has an apparatus such as an air displacement pump P. This pressure reduction means 16 keeps the inside of the electron beam irradiation area 11 being in a reduced-pressure state below the atmospheric pressure. Further, at least one sub area 12 is provided respectively on the carry-in side and the carry-out side of the sheet material 1 on the conveying path 10 adjacent to the electron beam irradiation area. Each of the sub areas 12 is connected to the pressure reduction means 16 via an exhaust system 18 that has an apparatus such as an air displacement pump P.

Figure 4:
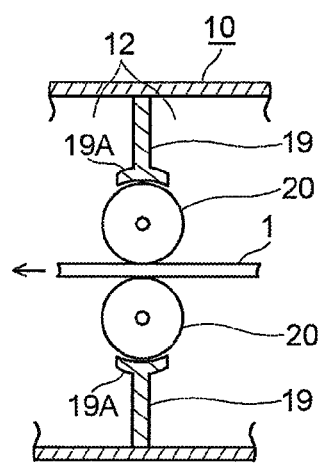
FIG. 4 is a sectional side view of another example of a hollow box-shaped conveying path.

As illustrated in FIG. 2 to FIG. 4 that schematically detail the hollow box-shaped conveying path 10, the sub area 12 can be formed by comparting with an upper and a lower partition walls 19 fixed inside the conveying path 10 and a roller 20 that is driven by a motor M with a minute gap involved. Or instead, the sub area 12 for a specific area may be formed only with the partition wall 19 with a minute gap still involved.

In the example illustrated in FIG. 3, the partition wall 19 for defining the sub area 12 is not given any significant working at its distal portion that faces the roller 20, which carries a sheet material 1, interleaving a minute gap therebetween. In the example illustrated in FIG. 4 in contrast, the partition wall 19 is provided with an arc-shaped element 19A at its distal end face that faces the roller 20 interleaving a minute gap therebetween. The example in FIG. 4 intends to make the width of the gap-area of the minute gap provided between the arc-shaped element 19A and the roller 20 can cover more widely than that in the example in FIG. 3 by enlarging the arc-shaped portion on the arc-shaped element 19A.

Providing at least one sub area 12 adjacent to the electron beam irradiation area 11 requires no particular sealing mechanisms in partitioning because such configuration increases flow resistance from the sub area to the atmosphere similarly to the function of a labyrinth structure.

Thus, providing at least one sub area 12 respectively on the carry-in side and the carry-out side of the sheet material 1 constitutes a differential evacuation system, which can efficiently keep the electron beam irradiation area 11 at the specified pressure level of reduced-pressure state. Additionally, it is a practicable configuration to provide the sub areas 12 respectively on the carry-in side and the carry-out side of the sheet material 1 in a proper number that permits the electron beam irradiation area 11 to be able to maintain its reduced-pressure state within the specified range.

In the example of an electron beam device for sterilization illustrated in FIG. 1, three sub areas are provided on the carry-in side of the sheet material 1. With this configuration, the internal pressure of each of the sub areas 12 becomes dependent on its closeness to the electron beam irradiation area 11 varying from the atmospheric pressure down to the desired negative pressure; this feature functions as the pressure regulation zone.

Similarly, another three sub areas 12 are provided on the carry-out side of the sheet material 1. With this configuration, the internal pressure of each of the sub areas 12 becomes dependent on its closeness to the electron beam irradiation area 11 varying from the desired negative pressure to the atmospheric pressure; this feature can work as the pressure regulation zone.

Connecting both the exhaust system 17 and the exhaust system 18 to the pressure reduction means 16 for a forced evacuation makes the internal pressures of the electron beam irradiation area 11 and the sub areas 12 on the carry-in and on the carry-out sides of the sheet material 1 low below the atmospheric pressure. Particularly thereby, the inside of the electron beam irradiation area 11 is made to maintain its pressure-reduced state at the specified level because of the sub areas 12. As will be described later, the inside of the electron beam irradiation area 11 is configured so that its internal pressure will be maintained in a reduced-pressure state preferably at 10 Pa to 10,000 Pa for a good irradiation.

In the electron beam irradiation area 11 of the embodiment illustrated in FIG. 1, two electron beam irradiation means 14 are arranged across the sheet material 1 on both sides thereof, in which each of the electron beam irradiation means 14 is connected to a power supply device (not illustrated). Electron beam emitted from an electron beam source 15 of the electron beam irradiation means 14 irradiates the surface of the sheet material 1 through an irradiation window 14A made of a thin film of such as graphite sheet in the directions as indicated with arrows of dotted lines in the figure.

The electron beam is radiated toward the sheet material 1 in the electron beam irradiation area 11 kept at reduced-pressure state to sterilize both surfaces of the sheet material 1. Although the width of the electron beam irradiation area 11 illustrated in FIG. 1 is an example that has the same width as that of the conveying path 10, a reduced width narrower than the width of the conveying path 10 can be practicable to make the distance between two electron beam irradiation means 14 closer. This closer arrangement permits use of a low-energy electron beam irradiation means for a good sterilization of both surfaces of the sheet material 1.

When the electron beam irradiation means 11 is maintained in a reduced-pressure state, the attenuation of electron beam emitted from the electron beam irradiation means 14 considerably reduces. Thus, the electron range (range of flight) will be extended longer compared to that of in the atmosphere even in the case of a low-energy electron beam accelerated by a low acceleration voltage. Further, the divergence of the electron beam is small and therefore an effective irradiation and sterilization of both surfaces of the sheet material 1 is attainable.

What is illustrated in FIG. 1 is an example in which two electron beam irradiation means 14 are arranged in the electron beam irradiation area 11. However, arranging one electron beam irradiation means 14 on one side of the electron beam irradiation area 11 is feasible because electron beam can penetrate the sheet material 1 with acceptable sterilization effect. With this single-side arrangement, a sterilization device can be manufactured more economically because the sterilization can be completed by irradiating only one side of the sheet material 1 with electron beam from a single electron beam irradiation means 14.

The acceleration voltage of electron beam of the electron beam irradiation means 14 in present invention is about 30 kV to 120 kV, preferably lower than 70 kV. Using the electron beam irradiation means 14 with this voltage generates less X-rays. Therefore, an X-ray shield of the electron beam irradiation area 11 or of the electron beam irradiation means 14 can be simplified or omitted.

In the example illustrated in FIG. 1, one pressure reduction means 16 evacuates the electron beam irradiation area 11 and the exhaust systems 17 and 18 of the sub areas 12 provided on the carry-in and the carry-out sides of the sheet material 1, being connected to all of them. The pressure reduction means 16 is applied considering leakage to the outside through the minute gap on the sub area 12 and the evacuation capacity of each pressure reduction means. The electron beam irradiation area 11 and at least one of the sub areas 12 on the carry-in and the carry-out sides may be connected severally to separate evacuation means; instead, the evacuation means may be commonly used to them as far as practicable.

In the present invention, a gas area 13 is provided adjacent to the sub area 12 located close to the atmosphere side of the carry-out side of the sheet material 1. This gas area 13 is defined with a partition wall 23 and a roller 24 in a manner similar to the sub area 12 stated above. The gas area 13 connects to a clean air supply means 21 such as a clean air generator, which has a properly selected filter, through a supply system 22 having a blower pump FP; thereby the gas area 13 is kept almost at the atmospheric pressure or higher.

The internal pressure of the electron beam irradiation area 11 in the conveying path 10 of the present invention is maintained by the pressure reduction means 16 within a range in which electron beam of a short electron range and a wide divergence is obtainable. When the sheet material 1 is processed with, for example, the low-energy electron beam irradiation means 14 that accelerates electrons at a voltage of 100 kV, the inside of the electron beam irradiation area 11 is controlled so that electron beam of a short electron range and an even spread (divergence) will be definitely obtained, using the pressure reduction means 16 that is capable of reducing an inner pressure down to a range of 10 kg to 80,000 kg.

The electron range is reversely proportional to the reduced internal pressure of the irradiation area. Therefore, when an electron beam emitted from the electron beam irradiation means 14 has such a property as is 5 cm in its range of flight under the atmospheric pressure, the emitted beam will become a divergent electron beam of which range is at most about 6.25 cm under a pressure of 80,000 Pa that is about four-fifth of the atmospheric pressure. Thus, this has an advantage in that such electron beam is suitable for uniform irradiation of a wider surface of the sheet material 1 and that the number of the irradiation windows to be provided in the irradiation area can be reduced.

Whether the internal pressure of the electron beam irradiation 11 is to be set within 10 Pa to 10,000 Pa should be properly determined according to operational conditions of each application. The operational conditions of each application includes kind of the sheet material 1 as the sterilization object, the electron range (range of flight) necessary to sterilize the sheet material 1, and the acceleration voltage and other particulars of the electron beam irradiation means 14.

Providing the gas area 13 on the conveying path 10 prevents germ invasion into the sub area 12 in the pressure regulation zone through the carry-out area from which the sterilized sheet material 1 is sent out. Thus, no anxiety about the adhering of germs to the sterilized sheet material 1 is left.

Accordingly, the sheet material 1 is transferred maintaining well its sterilized state into the subsequent process such as a carton forming process or a filling process for filling liquid food. Therefore, this configuration is applicable to a production line for carton-packed food without any difficulty.

The gas area 13 can be installed adjacent not only to the sub area 12 on the carry-out side of the sheet material 1 but also to the sub area 12 on the carry-in side of the sheet material 1. Further, this gas area 13 is also connected to the clean air supply means 21 through the supply system 22 having the blower pump FP; thereby the gas area 13 is kept almost at the atmospheric pressure or higher. With this configuration, the germ invasion into the sub area 12 on the carry-in side can be likewise prevented.

Installation of the gas area 13 on the carry-in side is to be determined considering the fact that the sheet material 1 that is transferred through the sub area 12 on the carry-in side is sterilized resultingly in the electron beam irradiation area 11 even the material comes in germs adhered thereon.

Industrial Applicability

An electron beam irradiation apparatus for sterilizing sheet material by the present invention has an electron beam irradiation area defined in a part of a hollow box-shaped conveying path and an electron beam irradiation means arranged in the electron beam irradiation area to face at least one surface of a sheet material. Therefore, the invented device is applicable to a processing in which at least one surface of a sheet material is sterilized with electron beam from an electron beam irradiation means. The electron beam irradiation area is kept at the reduced-pressure state of 10 Pa to 80,000 Pa by a pressure reduction means. At least one sub area is provided respectively on the carry-in side and the carry-out side of the sheet material on the hollow box-shaped conveying path adjacent to the electron beam irradiation area and a pressure reduction means that reduces the pressure of the sub area is provided. These features permit a sheet material for food packages to be well sterilized with a low-energy electron beam irradiation means and are suitable for the economical manufacturing of devices for such purpose.

The invention claimed is:

1. An electron beam irradiation apparatus for sterilizing a sheet material comprising:
   a conveying path configured for transferring a sheet material continuously;
   an electron beam irradiation means arranged on the conveying path so as to face at least one surface of the sheet material and provide sterilizing radiation to the surface of the sheet material with an electron beam;
   a clean gas supply means,
   wherein the electron beam irradiation means is arranged on an electron beam irradiation area in a part of the conveying path, and
   a pressure reduction means configured to maintain the electron beam irradiation area in a reduced-pressure state from 10 Pa to 10,000 Pa,
   wherein the conveying path is given a hollow box-shape to enclose the sheet material,
   at least one sub-area is provided respectively on the carry-in side and the carry-out side of the sheet material on the hollow box-shaped conveying path adjacent to the electron beam irradiation area,
   the pressure reduction means reduces the internal pressure of the sub-area, and
   the clean gas supply means feeds clean gas to a gas area, the gas area being located at least on the outer side of the sub-area of the carry-out side of the hollow box-shaped carrying path at the farthest end from the electron beam irradiation area.

2. The electron beam irradiation apparatus for sterilizing a sheet material according to claim 1,
   wherein the sub-area and the gas area include a partition wall fixed inside the conveying path and a roller that carries the sheet material.

* * * * *